United States Patent [19]

Noiles et al.

[11] Patent Number: 5,282,864
[45] Date of Patent: Feb. 1, 1994

[54] ACETABULAR PROSTHESIS HAVING A METAL SOCKET BEARING

[75] Inventors: Douglas G. Noiles, New Canaan; Alfred F. DeCarlo, Jr., Stamford, both of Conn.

[73] Assignee: Joint Medical Products Corporation, Stamford, Conn.

[21] Appl. No.: 838,090

[22] Filed: Feb. 19, 1992

[51] Int. Cl.$^5$ ............................................. A61F 2/34
[52] U.S. Cl. ...................................... 623/18; 623/22
[58] Field of Search ........................ 623/18, 19, 22, 23

[56] References Cited

U.S. PATENT DOCUMENTS

| | | |
|---|---|---|
| Re. 28,895 | 7/1976 | Noiles . |
| 3,820,167 | 6/1974 | Sivash . |
| 3,848,272 | 11/1974 | Noiles . |
| 3,943,576 | 3/1976 | Sivash . |
| 4,077,070 | 3/1978 | Sivash . |
| 4,678,472 | 7/1987 | Noiles . |
| 4,969,910 | 11/1990 | Frey et al. . |
| 4,978,356 | 12/1990 | Noiles ................... 623/18 |
| 5,080,679 | 1/1992 | Pratt et al. .................... 623/23 |
| 5,181,929 | 1/1993 | Prats et al. .................... 623/23 |

FOREIGN PATENT DOCUMENTS

WO 83/02555 8/1983 PCT Int'l Appl. .

OTHER PUBLICATIONS

Gates Power-Grip Timing Belt Catalog, 1988, pp. 14-15.

*Primary Examiner*—Randall L. Green
*Assistant Examiner*—Mary Beth Jones
*Attorney, Agent, or Firm*—Maurice M. Klee

[57] ABSTRACT

An acetabular prosthesis (8) having an orientable metal socket bearing (13) and a cup (10) for fixation to bone (6) is provided. The bearing (13) has a male taper (26) which locks into a corresponding female taper (28) formed in the cup (10). Two screws (15) are used to seat the bearing (13) in the cup (10) and to further secure the taper lock. The assembly of the apertures (4) through which bone screws (15) can pass to further secure the cup (10) to the patient's bone (6).

20 Claims, 2 Drawing Sheets

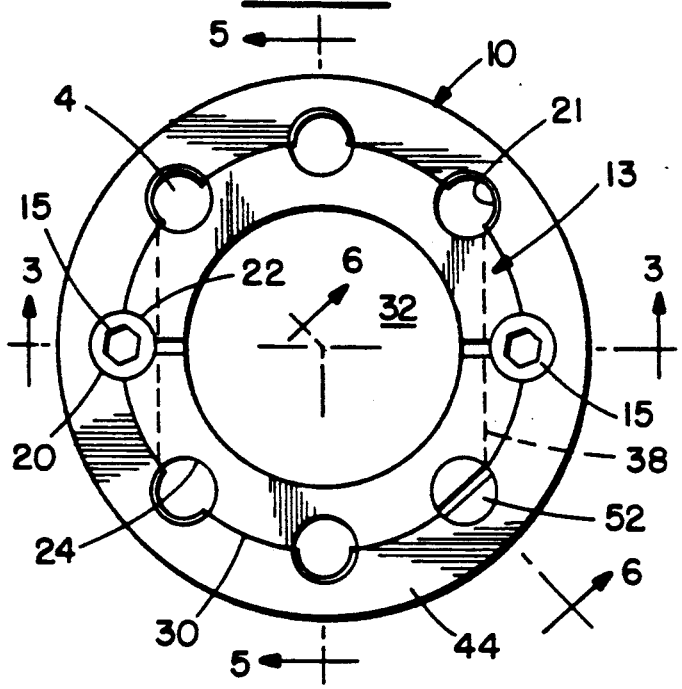
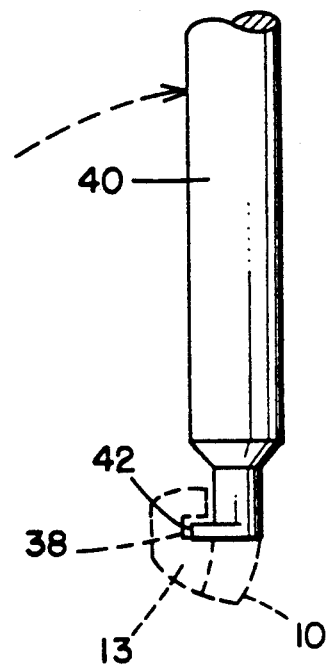
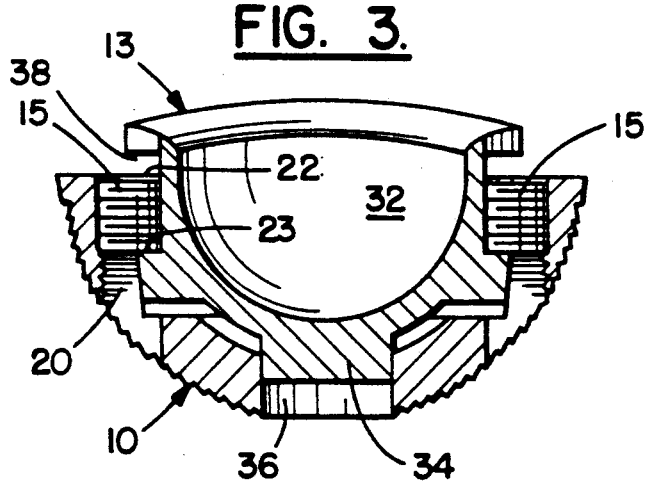
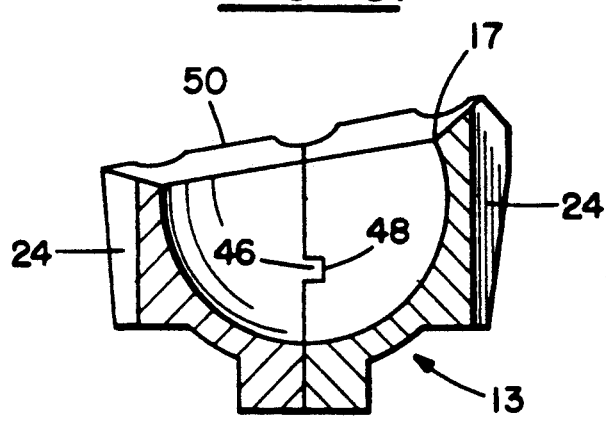
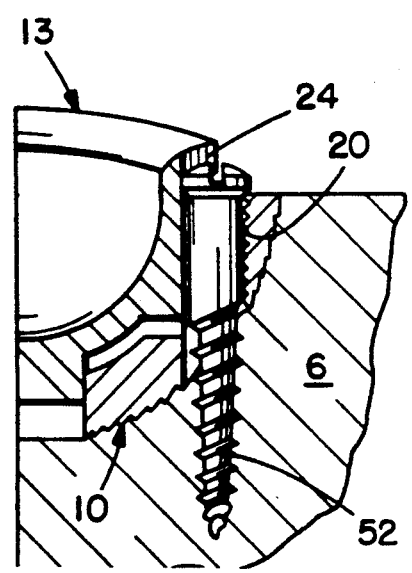

ACETABULAR PROSTHESIS HAVING A METAL SOCKET BEARING

BACKGROUND OF THE INVENTION

1. Field of the Invention

This invention relates to acetabular prostheses having metal socket bearings and, in particular, to an improved mechanism for affixing a metal socket bearing to an acetabular cup.

2. Description of the Prior Art

Acetabular prostheses having metal socket bearings are known in the art. Early constructions are shown in Sivash, U.S. Pat. Nos. 3,820,167, 3,943,576, and 4,077,070, and Noiles, U.S. Pat. Nos. 3,848,272, and Re 28,895. These prostheses were of the constrained type wherein the bearing encompassed more than half of the ball. The bearing consisted of two pieces which were placed around the ball and secured to the cup by riveting or screw threads. Because of the difficulty of assembling the prosthesis in situ, the surgeon was provided with an assembled joint comprising both the femoral and acetabular components.

PCT Patent Publication No. WO 83/02555 shows a variation of these earlier constructions wherein the metal bearing could encompass 180° or less of the femoral ball. Attachment between the bearing and the cup was again by means of a screw thread. Accordingly, although in situ assembly was not impossible, it was still generally impractical because of the screw thread.

Noiles, U.S. Pat. No. 4,678,472, shows two metal bearing constructions. In the first construction (FIGS. 9-10 of the '472 patent), the bearing comprises two pieces which encompass more than half of the ball and which are held together around the ball by means of retaining ring 74. For this construction, in the assembled joint, the bearing can rotate within the cup to provide a greater range of motion for the joint. In the second construction (FIGS. 33-34 of the '472 patent), the bearing again comprises two parts which in this case are locked in place within the cup by wedge 136.

Other constructions for acetabular prostheses employing metal socket bearings are disclosed in Frey et al., U.S. Pat. No. 4,969,910.

SUMMARY OF THE INVENTION

In view of the foregoing state of the art, it is an object of this invention to provide an improved acetabular prosthesis having a metal socket bearing. More particularly, it is an object of the invention to provide an improved mechanism for attaching a metal socket bearing to an acetabular cup which 1) essentially eliminates micro-motion between the bearing and the cup, 2) allows the metal bearing to be easily oriented with respect to the acetabular cup after the cup has been affixed to bone, 3) can be used with both constrained and non-constrained bearing configurations, and 4) allows for easy removal of the metal bearing from the cup.

To achieve the foregoing and other objects, the invention provides an acetabular prosthesis which comprises:

(a) an orientable metal socket bearing whose external surface includes a male taper: and (b) a metal cup for fixation to bone which includes a cavity for receiving the metal socket bearing, the surface of the cavity including a female taper for locking engagement with the male taper of the socket bearing.

In certain preferred embodiments of the invention, a set screw mechanism employing non-threaded, partial-length slots formed in the bearing and threaded, full-length slots formed in the cup, is used to seat the bearing in the cup and to further secure the taper lock. In other preferred embodiments, the bearing includes non-threaded, full-length slots which align with the threaded, full-length slots of the cup to form apertures which can receive bone screws to further secure the cup to the patient's bone.

The metal socket bearing preferably includes a lip to help restrain dislocations of the ball. Also, the bearing can encompass either less than or more than half the ball to produce a non-constrained or constrained construction, respectively. In the latter case, the bearing is composed of two pieces and preferably includes alignment means to aid in the assembly of the prosthesis.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

BRIEF DESCRIPTION OF THE DRAWINGS

FIG. 2 is a top view of the assembled prosthesis of FIG. 1.

FIG. 3 is a cross-sectional view along lines 3—3 in FIG. 2 showing the use of a set screw to seat the metal socket bearing insert in the cup.

FIG. 4 shows an instrument for use in loosening the metal socket bearing from the cup.

FIG. 5 is a cross-sectional view along lines 5—5 in FIG. 2 illustrating the application of the invention to a constrained, two-piece, metal socket bearing insert.

FIG. 6 is a cross-sectional view along lines 6—6 in FIG. 2 showing the use of a bone screw to fasten the cup to bone.

DESCRIPTION OF THE PREFERRED EMBODIMENTS

Figure 1:
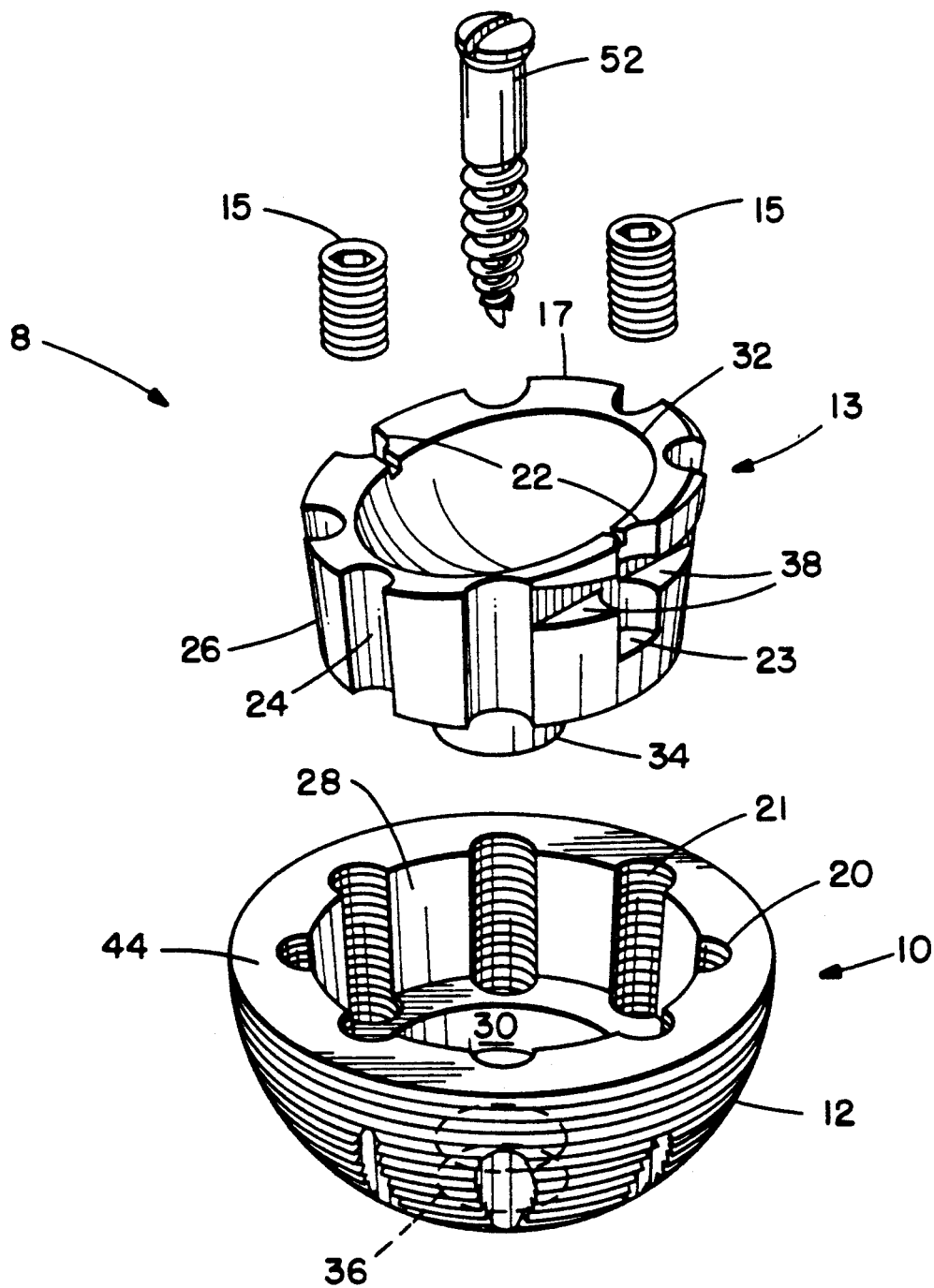
FIG. 1 is an exploded view of a prosthesis constructed in accordance with the invention and comprising a metal socket bearing insert, a cup, set screws, and bone screws.

With reference now to the drawings, wherein like reference characters designate like or corresponding parts throughout the several views, there is shown in FIG. 1 an exploded view of an acetabular cup 10 and a metal socket bearing 13 constructed in accordance with the invention.

Bearing 13 includes cavity 32 for receiving the ball of the femoral portion of the prosthesis. To aid in restraining dislocations of the ball, the bearing includes lip 17. During implantation, the lip is oriented in a direction which provides a range of motion and level of stability which best fits the anatomy of the patient. Preferably, a family of bearings having lips of different angular offsets is provided to the surgeon so that a suitable match can be achieved between the function of the prosthesis and the needs of the patient. See Noiles, U.S. Pat. No. 4,678,472.

Acetabular cup 10 includes outer surface 12 for engagement with bone and inner cavity 30 for receiving bearing 13. Various constructions known in the art can be used for outer surface 12. A particularly preferred construction is that disclosed in commonly assigned, Noiles and DeCarlos, U.S. patent application Ser. No. 07/838,577, entitled "Sintered Coatings for Implantable Prostheses", which is being filed simultaneously herewith.

Bearing 13 and cup 10 mate by means of a precise male taper 26 formed on the outside surface of the bearing and a precise female taper 28 formed on the inside surface of cavity 30. To ensure a secure fit between these components, the taper angle is chosen to be within the range of self-locking tapers. For example, a total included taper angle (both sides of the taper) in the range of from about 6° to about 17° will achieve this result To allow for removal of the bearing from the cup, the taper angle is preferably chosen towards the high end of the range of locking tapers. In practice, a total included taper angle of about 14° has been found to work successfully.

To ensure security of the locking taper, set screws 15 are used to seat bearing 13 in cup 10. The set screws operate by means of slots 22 formed in the outer surface of bearing 13 and slots 20 formed in the inner surface of cup 10. Slots 20 include threads 21 which engage the threads of set screws 15. Slots 22, which are unthreaded, include end surfaces 23 against which set screws 15 abut. As the set screws are tightened, they force bearing 13 into cup 10 by pushing against surfaces 23 thereby locking tapers 26 and 28 together (see FIG. 3).

As shown in FIGS. 1 and 2, bearing 13 includes two diametrically-opposed, non-threaded slots 22 having end surfaces 23. To avoid binding of the tapers, set screws 15 are preferably tightened against end surfaces 23 in alternating increments. If desired, additional slots 22 and set screws 15 can be used. Again, an alternating pattern for tightening the screws should be used. A single set screw can also be employed but, in general, is not preferred.

Threaded slots 20 in cup 10 are preferably arranged in multiple sets of diametrically-opposed slots with which the non-threaded slots 22 of bearing 13 can be aligned. In this way, the bearing can be readily oriented with respect to the cup and then secured to the cup in the selected orientation. For example, in FIG. 1, cup 13 includes four sets of diametrically-opposed threaded slots 20. Accordingly, bearing 13 has eight orientations with respect to cup 10. Of course, more or fewer sets of threaded slots 20 can be used as desired to achieve more or fewer possible orientations of the bearing with respect to the cup.

To aid in the assembly of bearing 13 and cup 10, the bearing preferably includes pilot hub 34, and the cup includes mating aperture 36 (see FIG. 3). The hub and aperture will preferably engage prior to the engagement of tapers 26 and 28 and thus prevent cocking of the bearing in the cup. Also, hub 34 can conveniently be used as a holding point during machining of the bearing. Likewise, aperture 36 can be used by the surgeon as a seat for an implantation instrument, as well as a viewing port. The inclusion of threads in aperture 36 can further facilitate implantation, as well as manufacture of the cup.

As can best be seen in FIGS. 1 and 3, bearing 13 includes notches 38 adjacent to non-threaded slots 22. These notches are used to unseat taper 26 from taper 28 in order to allow either rotation of the bearing within the cup or complete removal of the bearing if desired. In the assembled prosthesis, notches 38 sit proud of the face 44 of cup 10 (see FIG. 3), and thus can be engaged by tang 42 of loosening instrument 40 (see FIG. 4). Once engaged, the tang is used to pry the bearing free from the cup.

Other loosening techniques may be employed if desired such as the placement of full-length, threaded slots on bearing 13 and cooperating partial-length, non-threaded slots on cup 10. The turning of a set screw in this combination will drive the bearing out of, rather than into, the cup. Mechanisms of this type have been employed to disengage pulleys or gears from shafts upon which they have been mounted using a taper lock and set screw mechanism. See Gates Power-Grip Timing Belt Catalog, 1991, pages 72 and 82.

FIG. 5 shows an embodiment of the invention wherein the bearing is made in two halves and thus can be used to form a constrained prosthesis, i.e., a prosthesis wherein the bearing surrounds more than half the ball. The bearing construction used for this embodiment is essentially identical to that of FIGS. 1-3 except for the division of the bearing body into two parts. To assure alignment of the parts, key 46 is formed on one half and a mating slot 48 is formed in the other. This key and slot arrangement in conjunction with the halves being seated in taper 28 of the cup ensures the continuity of spherical cavity 32 in the assembled prosthesis. As shown in FIG. 5, bearing 13 has an oblique face 50 which forms lip 17. If desired, a scalloped perimeter of the type shown in FIG. 33 of U.S. Pat. No. 4,678,472 can be used in both this embodiment and that of FIGS. 1-3.

In addition to non-threaded, partial-length slots 22, bearing 13 (whether constrained or non-constrained) includes non-threaded, full-length slots 24. When slots 22 are aligned with one of the sets of slots 20 in cup 10, full-length slots 24 also align with slots 20. In this way, bone screws 15 can be inserted through the apertures formed by the alignment of slots 20 and 24.

In order for the heads of the bone screws to be recessed below the face 50 of bearing 13 and engage with cup 10, slots 24 have a diameter slightly greater than that of the head of the screw. In order for the bone screw to not pass through slot 20, the diameter of the screw head must be greater than the minor diameter of screw thread 21 in slot 20 and is preferably the same diameter as the major diameter of screw thread 21. In this way, the head of screw slides within slot 24 of the bearing and engages the cup at the end of thread 21 adjacent to face 44 of cup 10 (see FIG. 6). Typical diameters for the slots and bone screws which will achieve this result are: slot 24—0.262"; minor diameter of screw thread 21—0.201": major diameter of screw thread 21—0.242"; screw head—0.250" and maximum diameter of bone screw body—0.197". Other dimensions can of course be used if desired.

The components of the prosthesis can be constructed of various biocompatible metals known in the art. Preferably, the bearing is a cobalt-chromium alloy (see ASTM-F75 and ASTM-F799) and the cup is pure titanium or a titanium alloy such as Ti 6Al 4V (see ASTM-F136). The bone screws and set screws are preferably a Ti 6Al 4V alloy, although other materials can be used.

As is known in the art, fretting can take place where two metal parts meet if motion, including motion at the micron level (micro-motion), takes place between the parts under repetitive cyclic loading. It is for this reason that a secure locking engagement is critical to the success of an acetabular prosthesis employing a metal socket bearing. The locking taper mechanism disclosed above in combination with the use of set screws to ensure secure seating of the tapers provides the necessary security against motion between the parts and thus overcomes the hazard of fretting during long term use of the prosthesis.

A variety of modifications which do not depart from the scope and spirit of the invention will be evident to persons of ordinary skill in the art from the disclosure herein. The following claims are intended to cover the specific embodiments set forth herein as well as such modifications, variations, and equivalents.

What is claimed is:

1. A prosthesis for use in forming an implantable ball and socket joint comprising:
   (a) a metal socket bearing having a cavity for receiving the ball of the ball and socket joint, said socket bearing having an external surface at least a portion of which comprises a male taper; and
   (b) a cup for fixation to bone, said cup having a cavity for receiving the metal socket bearing, said cavity having a surface at least a portion of which comprises a female taper for locking engagement with the male taper of the socket bearing,
   wherein said male and female tapers comprise a self-locking taper.

2. The prosthesis of claim 1 wherein the total included taper angle of the locking male and female tapers is between about six degrees and about seventeen degrees.

3. The prosthesis of claim 2 wherein the total included taper angle of the locking male and female tapers is about fourteen degrees.

4. The prosthesis of claim 1 further including means for driving the male taper into the female taper.

5. The prosthesis of claim 4 wherein the means for driving comprises a screw.

6. The prosthesis of claim 5 wherein the bearing includes a non-threaded slot having an open end and a closed end, the cup includes a threaded-slot, and the screw is received in an aperture formed by alignment of the non-threaded slot with the threaded slot.

7. The prosthesis of claim 6 wherein the cup includes a second threaded slot and the bearing includes a non-threaded slot having two open ends which can cooperate with the second threaded slot of the cup to form an aperture which will allow passage of the body but not the head of a bone screw.

8. The prosthesis of claim 7 wherein the thread of the second threaded slot prevents passage of the head of the bone screw through the aperture.

9. The prosthesis of claim 6 wherein the cup includes a plurality of threaded slots and the non-threaded slot of the bearing can be aligned with any one of said threaded slots to form an aperture for the screw.

10. The prosthesis of claim 9 wherein the bearing includes a non-threaded slot having two open ends which can cooperate with a threaded slot of the cup to form an aperture which will allow passage of the body but not the head of a bone screw.

11. The prosthesis of claim 10 wherein the thread of the threaded slot prevents passage of the head of the bone screw through the aperture.

12. The prosthesis of claim 1 including means for loosening the locking engagement between the male taper of the bearing and the female taper of the cup.

13. The prosthesis of claim 12 wherein the means for loosening comprises a groove formed in the external surface of the bearing.

14. The prosthesis of claim 1 wherein the metal socket bearing comprises two pieces.

15. The prosthesis of claim 14 including means for aligning the two pieces of the metal socket bearing.

16. The prosthesis of claim 15 wherein the means for aligning comprises a key on one of the pieces and a slot on the other piece.

17. A prosthesis for use in forming an implantable ball and socket joint comprising:
   (a) a metal socket bearing having a cavity for receiving the ball of the ball and socket joint, said socket bearing having an external surface which includes a first non-threaded slot having an open end and a closed end and a second non-threaded slot having two open ends: and
   (b) a cup for fixation to bone, said cup having a cavity for receiving the metal socket bearing, said cavity having a surface which includes two threaded slots wherein alignment of the first non-threaded slot of the bearing with one of said threaded slots forms a first aperture for a set screw and the alignment of the second non-threaded slot of the bearing with the other of said threaded slots forms a second aperture for a bone screw.

18. The prosthesis of claim 17 wherein the second aperture will allow passage of the body but not the head of a bone screw.

19. The prosthesis of claim 18 wherein the thread of the other threaded slot prevents passage of the head of the bone screw through the aperture.

20. A prosthesis for use in forming an implantable ball and socket joint comprising:
   (a) a metal socket bearing having a cavity for receiving the ball of the ball and socket joint, said socket bearing having an external surface which includes a first non-threaded slot having an open end and a closed end and a second non-threaded slot having two open ends; and
   (b) a cup for fixation to bone, said cup having a cavity for receiving the metal socket bearing, said cavity having a surface which includes a plurality of threaded slots wherein alignment of the first non-threaded slot of the bearing with one of said threaded slots forms a first aperture for a set screw and the alignment of the second non-threaded slot of the bearing with another of said threaded slots forms a second aperture for a bone screw.

* * * * *